(12) United States Patent
Hayden (10) Patent No.: US 10,776,610 B2
(45) Date of Patent: Sep. 15, 2020

(54) SYSTEM FOR MONITORING FACIAL PRESENTATION OF USERS

(71) Applicant: Ruth Ellen Cashion LLC, Wetumpka, AL (US)

(72) Inventor: Steven Mark Hayden, Wetumpka, AL (US)

(73) Assignee: RUTH ELLEN CASHION LLC, Wetumpka, AL (US)

( * ) Notice: Subject to any disclaimer, the term of this patent is extended or adjusted under 35 U.S.C. 154(b) by 103 days.

(21) Appl. No.: 16/130,812

(22) Filed: Sep. 13, 2018

(65) Prior Publication Data

US 2019/0087649 A1 Mar. 21, 2019

Related U.S. Application Data

(60) Provisional application No. 62/559,392, filed on Sep. 15, 2017.

(51) Int. Cl.
| | | |
|---|---|---|
| *G06K 9/00* | (2006.01) | |
| *A42B 1/24* | (2006.01) | |
| *A61B 5/00* | (2006.01) | |
| *G06T 7/70* | (2017.01) | |
| *A61B 5/16* | (2006.01) | |
| *G09B 19/00* | (2006.01) | |

(52) U.S. Cl.
CPC .......... *G06K 9/00288* (2013.01); *A42B 1/245* (2013.01); *A61B 5/0077* (2013.01); *A61B 5/165* (2013.01); *A61B 5/4064* (2013.01); *A61B 5/6803* (2013.01); *G06K 9/00302* (2013.01); *G06T 7/70* (2017.01); *G09B 19/00* (2013.01)

(58) Field of Classification Search
CPC ....... A61B 5/165; A61B 5/6803; A61B 5/163; A61B 5/7267; G06F 1/163; G06F 3/011; G06K 9/00302; G06K 9/00362; H04N 7/185; H04N 5/23219; H04N 21/41407; H04N 21/44218; G06T 2207/30201; G06T 1/0007; G06T 2207/30196
See application file for complete search history.

(56) References Cited

U.S. PATENT DOCUMENTS

| | | | | |
|---|---|---|---|---|
| 8,687,925 B2* | 4/2014 | Sano | ...................... | A61B 5/165 382/305 |
| 10,024,667 B2* | 7/2018 | Moore | ................. | G01C 21/165 |

(Continued)

*Primary Examiner* — Dung Hong (57) ABSTRACT

Disclosed is a system for monitoring facial presentation of a first user to a second user. The system may include at least one image capturing device configured for capturing at least one image of the first user. Further, the system may include a communication device communicatively coupled to the at least one image capturing device. Further, the system may include a processing device communicatively coupled to the communication device. The communication device may be configured for transmitting the at least one image to a processing device. The processing device may be configured for analyzing the at least one image. The processing device may be configured for identifying a face of the first user based on the analyzing. Further, the processing device may be configured for generating facial presentation data based on the identifying. Further, the system may include a storage device configured for storing the facial presentation data.

18 Claims, 8 Drawing Sheets

(56) References Cited

U.S. PATENT DOCUMENTS

| | | | | |
|---|---|---|---|---|
| 2005/0004496 | A1* | 1/2005 | Pilu | H04N 5/232 600/595 |
| 2008/0273798 | A1* | 11/2008 | Asukai | G06K 9/00221 382/190 |
| 2009/0238419 | A1* | 9/2009 | Steinberg | H04N 5/2621 382/118 |
| 2013/0039483 | A1* | 2/2013 | Wolfeld | H04M 3/51 379/265.03 |
| 2013/0245396 | A1* | 9/2013 | Berman | G06F 19/3418 600/301 |
| 2014/0357976 | A1* | 12/2014 | Pitre | G16H 50/70 600/407 |
| 2015/0061824 | A1* | 3/2015 | Suzuki | G06F 3/013 340/5.52 |
| 2015/0099946 | A1* | 4/2015 | Sahin | G16H 10/65 600/301 |
| 2015/0223731 | A1* | 8/2015 | Sahin | A61B 5/0022 600/301 |
| 2017/0061200 | A1* | 3/2017 | Wexler | H04N 21/42203 |
| 2017/0319123 | A1* | 11/2017 | Voss | G16H 40/63 |
| 2017/0365101 | A1* | 12/2017 | Samec | A61B 5/4094 |
| 2018/0081365 | A1* | 3/2018 | Asukai | B25J 11/0005 |
| 2018/0114063 | A1* | 4/2018 | Wexler | G06T 1/0007 |
| 2018/0124299 | A1* | 5/2018 | Brook | H04N 5/23222 |
| 2019/0015033 | A1* | 1/2019 | Sahin | A61B 5/6803 |
| 2020/0026347 | A1* | 1/2020 | el Kaliouby | H04L 51/10 |

* cited by examiner

SYSTEM FOR MONITORING FACIAL PRESENTATION OF USERS

The current application claims a priority to the U.S. Provisional Patent application Ser. No. 62/559,392 filed on Sep. 15, 2017

FIELD OF THE INVENTION

The present disclosure relates generally to the field of learning systems. More specifically, the present disclosure relates to monitoring facial presentation of a first user to a second user.

BACKGROUND OF THE INVENTION

Busy working mothers often leave infants with teenage caregivers or at day care centers. In such situations, the infants may not be disturbed except for feeding and diaper changes. Further, the mother or the guardian cannot easily measure how much face-time the infant gets in such situations.

Often, day care centers have surveillance cameras that show the point of view of the adult observers in the room. The cameras mounted to a fixed position in the room, such as on a crib or on the walls, do not show the point of view of the infant. Therefore, the conventional infant monitoring systems do not make measurements from the point of view of the infant, such as measurements related to the face exposure to the infant for learning facial expression. Infants see and learn from properly presented faces in visual field. Infants learn facial expressions which is important for learning emotional communication Therefore, there is a need for an improved system for monitoring facial presentation of users that may overcome one or more of the above-mentioned problems and/or limitations.

SUMMARY

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, a system for monitoring facial presentation of a first user to a second user is disclosed. The system may include at least one image capturing device configured for capturing at least one image of the first user. Further, the system may include a communication device communicatively coupled to the at least one image capturing device. Further, the system may include a processing device communicatively coupled to the communication device. The communication device may be configured for transmitting the at least one image to a processing device. The processing device may be configured for analyzing the at least one image. The processing device may be configured for identifying a face of the first user based on the analyzing. Further, the processing device may be configured for generating facial presentation data based on the identifying. Further, the system may include a storage device configured for storing the facial presentation data.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of learning systems, embodiments of the present disclosure are not limited to use only in this context.

Overview

According to some embodiments, the present disclosure relates to a method for measuring the face exposure to the infant for learning facial expression. The infants see and learn from properly presented faces in their visual field. The infants see and learn facial expressions which helps in emotional communication. The disclosed method may be used to calculate the visual information presented in an infant's visual field. This may include measuring the distance from the infant's face. Further, the alignment of midline face in the visual field may be measured. The midline of face in the visual field splits the face into two symmetrical halves with an eye on each side of the vertical midline. The facial midline separates the two eye sockets and crosses from nasal root to midline of the mouth. This facial midline is aligned with the vertical midline of the visual field for best learning of the infant.

The recording and processing of the visual field of the infant allows for accurate measurement of facial data presented to infant and its alignment and distance. A face in the infant's visual field that occupies a smaller portion of the visual field or is angled is not as effective for teaching facial expression to infant. The disclosed method may measure both area of the visual field occupied by face and also measure time that face is in visual field. This may include placing a video monitor near the eyes of the infant facing forward into the infant's field of view.

According to an embodiment, a digital camera (such as a CMOS or CCD camera) may be aligned with a focal axis in the median plane of the infant's anatomy. The horizontal field of view of the digital camera may be fixed or may be moved (such as from 30-75 degrees). The camera may be able to focus at a distance between 12-24 inches. The digital image from a caregiver's face at distance of 12 inches (eye-to-eye face-to-face) looking directly at infant may be recorded. A facial box containing the facial landmarks recognized by a facial recognition software may be recorded as a yellow box, which may be projected and retained on the monitor. Further, a red box may be formed by the landmarks of the facial data of the caregiver when the face is held at distance of 18-22 inches or at arm's length. The red and yellow facial boxes may be retained on the monitor while live images from the infant mounted camera are displayed on the monitor. The environment does not allow the infant to see the monitor which represents the infant's point of view. The monitor with the infant's point of view may be seen by the caregiver so that she will know how she appears to the infant. Further, a recording of the digital visual facial data may be recorded under the control of an infant guardian. The caregiver's facial landmarks may form a facial box on the monitor. If the size of the caregiver's face is greater than arm's length, then the facial box may be smaller than the facial box at arm's length and the caregiver's face may not occupy most or all of the red or the yellow box. The effective facial display of caregiver's face may be recorded by the facial box that covers most or all of the red or the yellow box. The proper facial teaching requires the face of the caregiver to be properly presented to the visual field of infant.

For example, the breast fed mothers hold infant at an arm's length and have at least part of their face within the facial box while feeding. A loving caregiver may hold the infant in arms with her face aligned in the red or the yellow facial box. Further, loving and attentive caregivers may have higher facial box time for higher and better facial presentation duration and coverage.

However, bad caregivers may leave the infant in the crib staring at a ceiling with no face in the facial box. Further, resourceful caregivers may put the infant in front of mirror so the face on monitor is infant's face. According, the disclosed system is able to recognize the infant's face and exclude it from useful data recording the caregiver's face. The caregivers that do not have adequate face-time may be provided feedback such that they may either improve their behavior by learning to keep their face in the facial box or they may be replaced by the guardian.

According to an embodiment, an independent process to notify the caregiver when the face is in vertical midline of the infant field of view is disclosed. The infants rarely use their eyes to look far to their left or to their right. When concentrating on a face, the infant observes with the vertical midline of their field of view. In such cases, the vertical midline of the image splits the observed face into two symmetrical halves. The vertical midline is aligned parallel to the nasal ridge. When the vertical midline of facial box aligns with vertical midline of the camera image, a signal may be sent to either the caregiver or the infant. The signal may be sent through electromagnetic spectrum. For example, the signal may be used to turn on a LED light on the infant's head or to play an audio (such as a melody song). So, every time the face of the caregiver is properly presented to infant, a melody may be played and the LED light may be switched on to inform the caregiver the infant is receiving proper visual stimulation.

According to an embodiment, a camera may be mounted in a cap of an infant. The camera may be aligned with the visual field of the infant. Infants align their fovea (part of an eye) with the center of their attention. The infants may turn their body and head to face what the infant is interested in. Further, a facial box at a distance of 12 inches and arm's length (about 20 inches) may be determined. The visual data may be then displayed live to show that the visual data is being monitored. The caregiver may follow her measured face presentation in the red and yellow facial box. If the facial box is smaller than the red facial box at arm's length, then it may imply that the infant is not being held. The caregiver that neglects the infant will not appear in the monitor (or not cover most or all of the red or yellow facial box).

Further, additional feedback may be provided to the caregiver. For example, an electronic message may be sent to turn on a light on the infant's head. Alternatively, a vibration or an audible notification may be delivered. An earpiece in the caregiver's ear may receive the vibration or the audible notification.

Further, if the camera is not aligned with the median plane, then it may be moved until the tip of the nose is 18 inches anterior to the nose of the infant at the vertical and the horizontal midline of the monitor. This centering of the monitor may be done frequently, such as every 10-15 minutes.

In an embodiment, a camera (such as a CMOS or CCD camera) may be mounted in a head clothing, such as a headband or cap of the infant. The camera may be mounted and constructed such that it does not cause a choking hazard. Further, the camera with 20-60-degree horizontal field of view may be used. Further, facial recognition software may be used on the images captured by the camera mounted on the infant's head. Accordingly, a facial box or an area showing facial landmarks may be marked and recorded.

Further, a similar function may be performed by continuously recording with a facial box. However, the caregiver may be 6-feet out-of-reach while not holding the infant and her face may still appear in the visual field. Therefore, the face must be large enough in the visual field for useful information to be extracted by the infant. The infant must enter arm's length distance (or a shorter distance) from the caregiver and also make face contact with the face in the yellow or the red facial box.

According to a further embodiment, the caregiver may be rated based on their interaction with the infant. Further, the caregiver may be told how she is being rated and how she can improve. The caregiver may improve her face-time if she knows how to monitor face-time. The social services may use face-time as measure of maternal or caregiver interaction.

Further, if an infant pays no attention to human faces then infant may not turn head to bring a caregiver's face in the facial box. Autistic infants are likely to avoid close proximity and eye contact. The autistic infants have very poor face contact scores. An autistic 12-month-old infant may not often bring face into the facial box. At a young age, autistic infants do not move faces into the facial box. This is more difficult with autistic children at 2-3 years' age who may rip-off the head monitor. But for the younger infants (between 6-18 months) it is useful to mount a head camera to see how much face-time the infants get. Further, using food for reinforcing, the infants with autism may be fed when the head is turned towards the face of the mother or the caregiver. When the infant turns face towards the mother and overlaps the face with the facial box, the infant may be assigned a higher score. Until 3-4 months, the infants turn head and are completely dependent on the caregiver moving into visual field of the infant. Therefore, the disclosed system may be an effective tool for early detection of autism, and for monitoring caregivers to increase face contact and quality facial input. An attentive child at ages 6-18 months may turn their field of view towards a human face. Further, the total time for faces and individual faces in facial box may be recorded for analysis. The children that fail to get an adequate face-time may be monitored or receive therapy to increase their visual attention to parents and caregivers.

According to a further embodiment, a central field of view of the infant may be covered by face at a distance of 12-20 inches. The area of the image occupied by facial image may be calculated for each image. Each digital frame represents a moment in time. Usually each second of digital recording has 16-128 frames or more. The total number frames with the facial box may be calculated as measure of time that the face is properly represented. Alternatively, facial box analysis may be performed every fraction of a second. The greater the number of facial box images with the face, the greater time a face is adequately presented visual field of the infant.

According to a further embodiment, the disclosed system may include a privacy filter to exclude recording of data outside the facial box. For example, the family members and caregivers are sometimes partly or wholly naked in view of the infant. Therefore, the disclosed system may be configured to exclude transfer of information outside the facial box to protect privacy of the family members and the caregivers. Therefore, only the digital data that includes the face may be stored. Storing images with only faces do not violate most privacy standards. For example, video surveillance of private areas including bathrooms and bedrooms often has exposure of private naked body parts. Faces are not private and are not part of ordinary privacy standards. Other body parts are often private or used to create obscene offensive images invading privacy.

Figure 1:
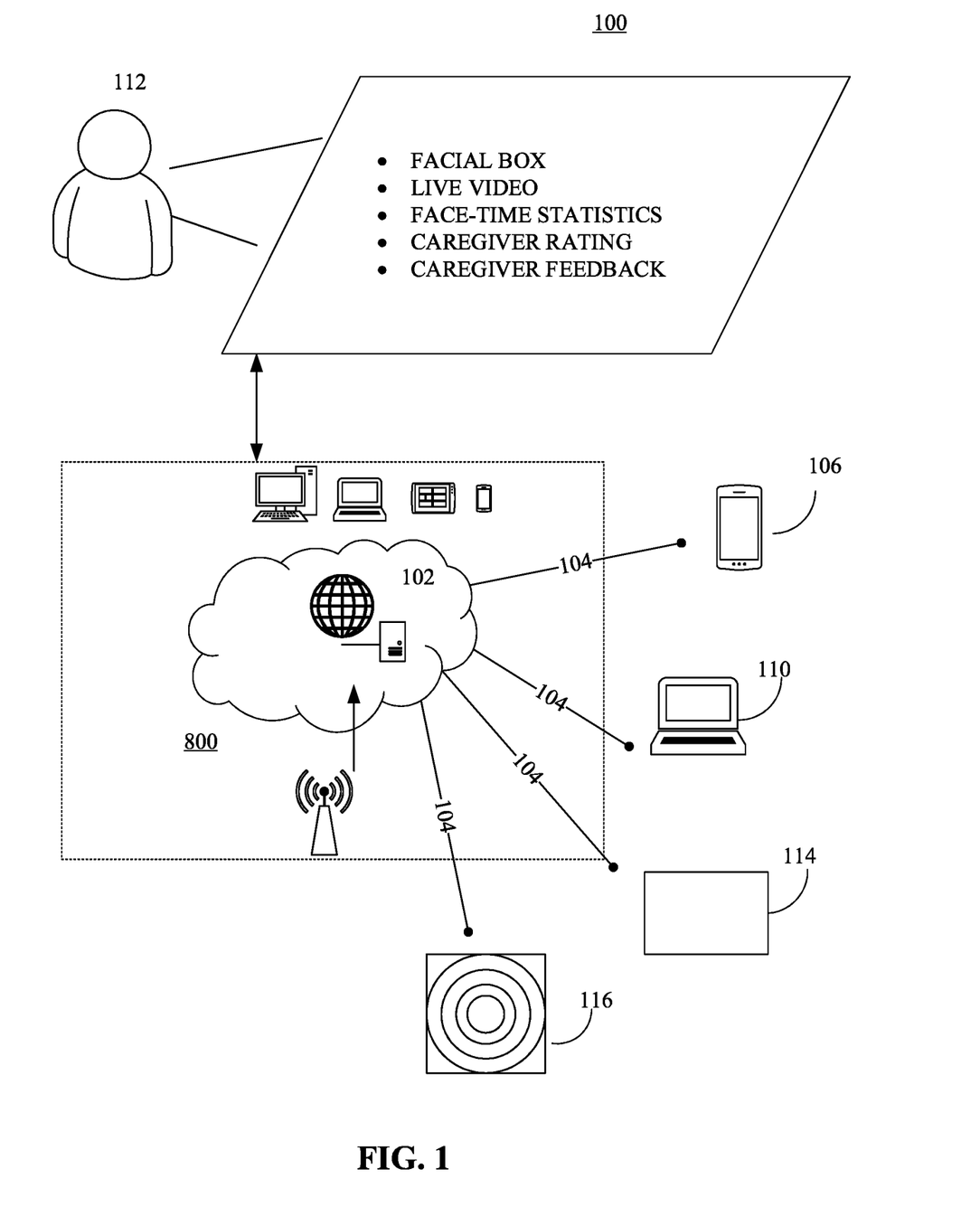
FIG. 1 is an illustration of an online platform consistent with various embodiments of the present disclosure.

Referring now to figures, FIG. 1 is an illustration of an online platform 100 consistent with various embodiments of the present disclosure. By way of non-limiting example, the online platform 100 for monitoring facial presentation of a first user to a second user may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), display devices 114 (such as an LED display, an LCD display, an OLED display), and sensors 116 (such as a camera sensor), over a communication network 104, such as, but not limited to, the Internet. Further, users of the online platform 100 may include relevant parties such as, but not limited to, babies, caregivers, parents, learners, teachers and administrators. Accordingly, in some instances, electronic devices operated by the one or more relevant parties may be in communication with the platform 100.

A user 112, such as the one or more relevant parties, may access online platform 100 through a web-based software application or browser. The web-based software application may be embodied as, for example, but not be limited to, a website, a web application, a desktop application, and a mobile application compatible with a computing device 800.

Figure 2:
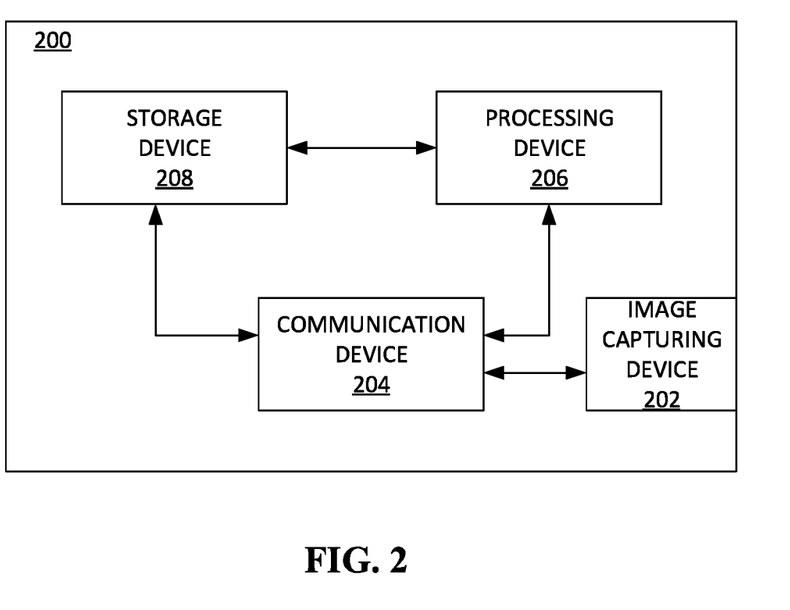
FIG. 2 is a block diagram of a system for monitoring the facial presentation of a first user to a second user, in accordance with some embodiments.

FIG. 2 is a block diagram of a system 200 for monitoring the facial presentation of a first user to a second user, in accordance with some embodiments. For example, the first user may be a caregiver (such as a babysitter) and the second user may be an infant. Infants see and learn from properly presented faces in their visual field. The system 200 may be used to measure the face exposure of the infant for learning facial expression. In another embodiment, the first user may be a coach (such as a body language coach) and the second user may be a learner.

The system 200 may include at least one image capturing device 202 configured for capturing at least one image of the first user. The at least one image capturing device 202 may a camera sensor in the sensors 116. In some embodiments, the at least one image capturing device 202 may be configured to be disposed proximal to at least one eye of the second user. This ensures that the field of view of the at least one image capturing device 202 is similar to the field of view of the second user. Accordingly, less computation is required to obtain the exact field of view of the second user.

Figure 3:
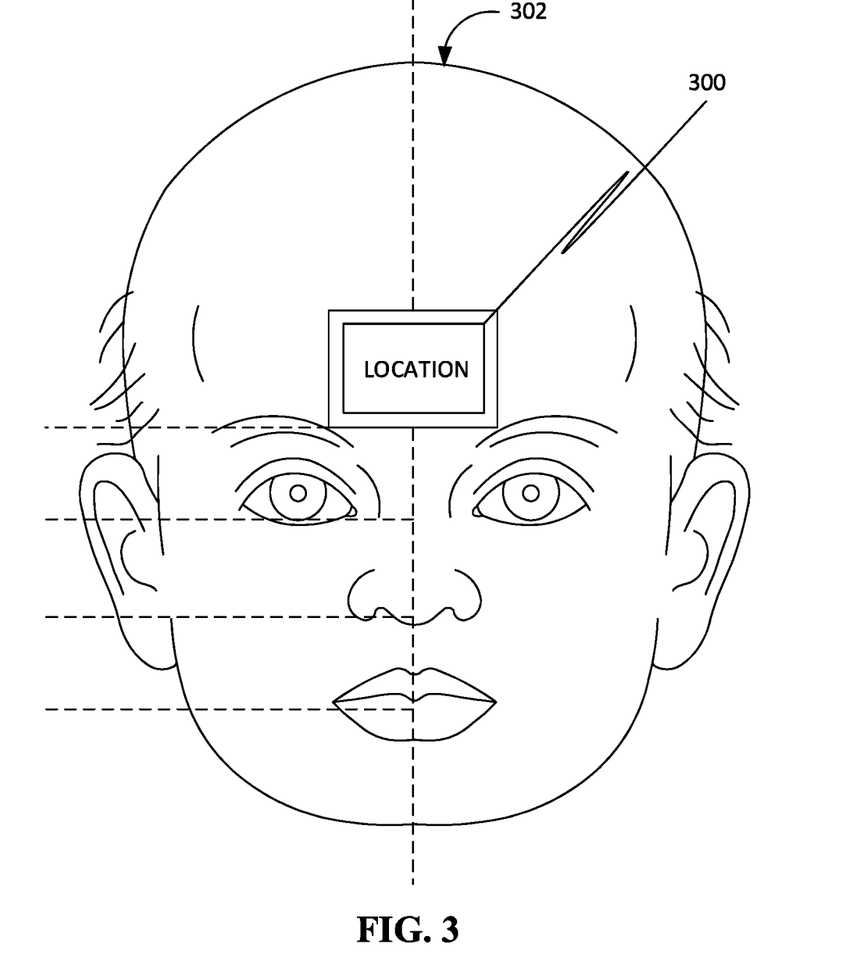
FIG. 3 illustrates a location for placement of at least one image capturing device in reference to a face of a user, in accordance with an embodiment.

Accordingly, the at least one image capturing device 202 may be configured to be disposed in the median plane (or the sagittal plane) of the second user as shown in FIG. 3. The median plane of infant anatomy divides the skull into two symmetric halves parallel to sagittal suture line of the skull. FIG. 3 illustrates a location 300 for placement of the at least one image capturing device 202 in reference to the face 302 of the second user (for example, an infant). As, shown, the location 300 is the portion of the forehead between the two eyebrows. When the at least one image capturing device 202 is placed in the location 300, the focal axis of the at least one image capturing device 202 aligns parallel with the median plane. The field of view of the at least one image capturing device 202 faces directly in front of the second user with vertical midline of field of view aligned with median plane.

Figure 4:
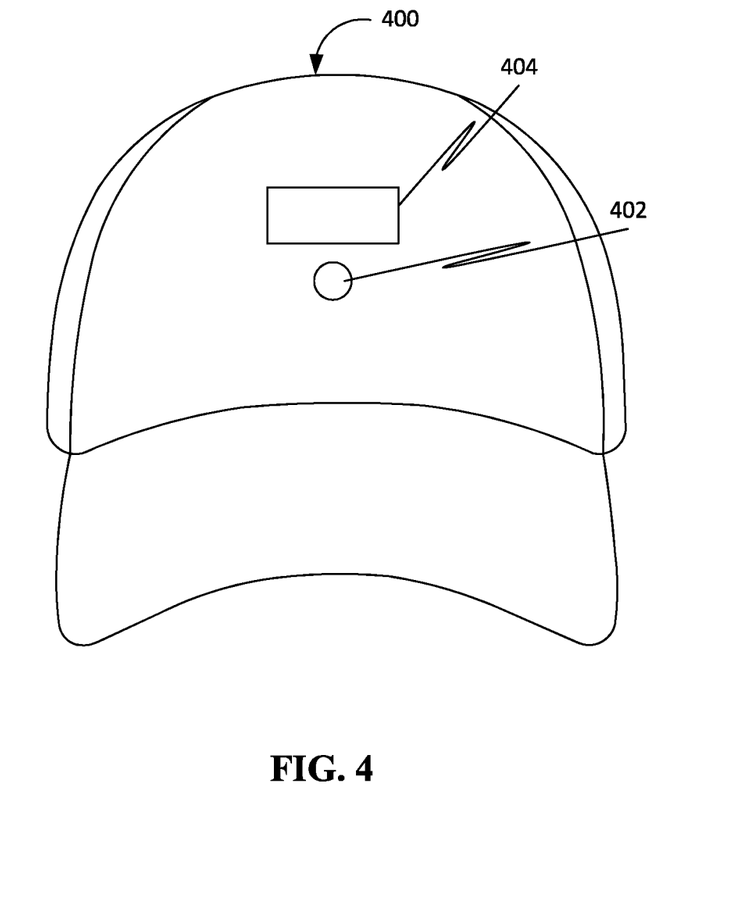
FIG. 4 illustrates a cap with a camera and a display, in accordance with an exemplary embodiment.
Figure 5:
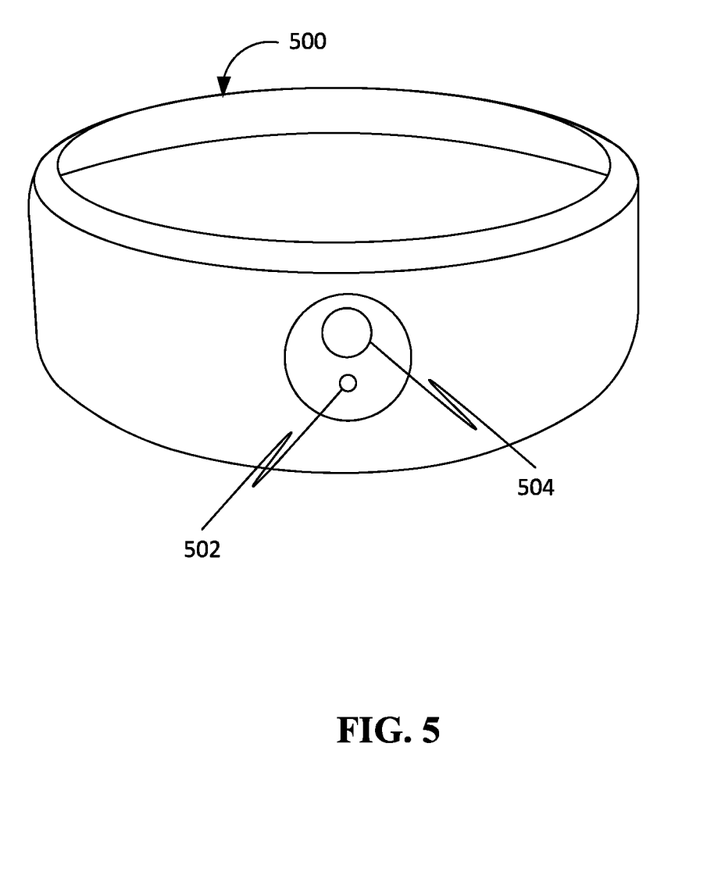
FIG. 5 illustrates a head band with a camera and a display, in accordance with an exemplary embodiment.

Further, the at least one image capturing device 202 may be comprised in a wearable article (such as a cap or a head band) configured to be worn by at least one of the first user and the second user. FIG. 4 illustrates a cap 400 with a camera 402 (the at least one image capturing device 202), in accordance with an exemplary embodiment. FIG. 5 illustrates a head band 500 with a camera 502 (the at least one image capturing device 202), in accordance with an exemplary embodiment.

Further, the system 200 may include a communication device 204 communicatively coupled to the at least one image capturing device 202. Yet further, the system 200 may include a processing device 206 communicatively coupled to the communication device 204. The communication device 204 may be configured for transmitting the at least one image to the processing device 206. Further, the processing device 206 may be configured for analyzing the at least one image. Moreover, the processing device 206 may be configured for identifying a face of the first user based on the analyzing. Further, the processing device 206 may be configured for generating facial presentation data based on the identifying. Further, the system 200 may include a storage device 208 configured for storing the facial presentation data.

In some embodiments, the facial presentation data may include an area of a visual field corresponding to the at least one image capturing device 202. Further, the area may be occupied by the face of the first user.

In some embodiments, the facial presentation data may include a time duration corresponding to the presence of the face of the first user in the visual field. Accordingly, it may be determined if the first user is providing enough face-time to the second user.

In some embodiments, the facial presentation data may include a location of the face of the first user within the visual field. For example, the preferred location of the face of the first user within the visual field may be the center of the visual field. Accordingly, the facial presentation data may be processed, using the processing device 206, to calculate a deviation of the face of the first user from the center of the visual field.

In some embodiments, the facial presentation data may include an orientation of the face of the first user within the visual field. For example, the preferred orientation of the face of the first user within the visual field may be the front face. Accordingly, the facial presentation data may be processed, using the processing device 206, to calculate a deviation of the face of the first user from the front face orientation.

In further embodiments, the facial presentation data may include an alignment indicator based on alignment between the face of the first user and a face of the second user.

In some embodiments, the system 200 may further include identifying at least one emotional expression associated with the face of the first user based on the analyzing. For example, the emotional expression of a caregiver may be identified. Further, the facial presentation data may include the at least one emotional expression. In further embodiments, the processing device 206 may be configured for determining at least one frequency corresponding to the at least one emotional expression. Further, the facial presentation data may include the at least one frequency.

In some embodiments, the system 200 may further include a distance sensor configured to measure a distance between the first user and the second user. Further, the generating of the facial presentation data may be based further on the distance. The distance between the first user and the second user may be used to determine the size of the face of the first user as viewed by the second user. For babies, it is important to see big sized faces so that they can learn facial features.

In some embodiments, the system 200 may further include a display device communicatively coupled to the processing device 206. Further, the display device may be configured to display one or more of the at least one image of the first user and the facial presentation data. For example, the cap 400 may include a display 404 and the head band 500 may include a display 504 to display one or more of the at least one image of the first user and the facial presentation data. For example, the display device may show the face of the caregiver as seen from infant's point of view. The display devices 114 may include the display 404 and the display 504.

Further, the facial presentation data may include at least one facial landmark. For example, the at least one facial landmark may include a circle shown on the display device along with the at least one image of the first user. The circle may indicate the ideal position of the face of the first user. The ideal position may be front face of the first user at a particular distance away from the second user.

In some embodiments, the processing device 206 may be further configured for analyzing the facial presentation data based on at least one predefined criterion and generating an alert based on the analyzing. Further, the communication device 204 may be further configured for transmitting the alert to a user device. For example, the at least one predefined criterion may be a threshold time period when the first user does not appear in the field of view of the second user. For example, it may be determined if the caregiver did not appear in the field of view of the infant for over an hour.

In some embodiments, the processing device 206 may be further configured for generating an audible message based on the facial presentation data. Further, the communication device 204 may be configured for transmitting the audible message to a user device associated with the first user. The audible message may allow the second user to easily position themselves based on the audible message(s), without the need of looking at the display device.

In some embodiments, the system 200 may further include at least one display device configured to be communicatively coupled to the communication device 204. Further, the display device may be further configured to be disposed on the second user. Further, the display device may be configured to display the facial presentation data.

In some embodiments, the facial presentation data may include the face of the first user, wherein the processing device 206 may be further configured for identifying at least one non-facial portion of the first user in the at least one image. Further, the processing device 206 may be configured for redacting the at least one image based on the identifying of the at least one non-facial portion. This may help is protecting privacy of the first user. Yet further, the processing device 206 may be configured for generating at least one redacted image based on the redacting. Further, the storage device 208 may be configured for storing the at least one redacted image.

In some embodiments, the at least one image capturing device 202 may be further configured for capturing at least one image of the second user. Further, the processing device 206 may be configured for analyzing the at least one image of the second user, identifying a face of the second user based on the analyzing of the at least one image of the second user and generating facial response data based on the identifying of the face of the second user. Further, the storage device 208 may be further configured for storing the facial response data.

In further embodiments, the processing device 206 may be configured for comparing the facial presentation data with the facial response data and diagnosing a behavioral disorder based on the comparing. For example, the facial response of the infant may be compared with the facial expressions of the caregiver, to diagnose a behavioral disorder (such as early stage autism) in the infant.

Figure 6:
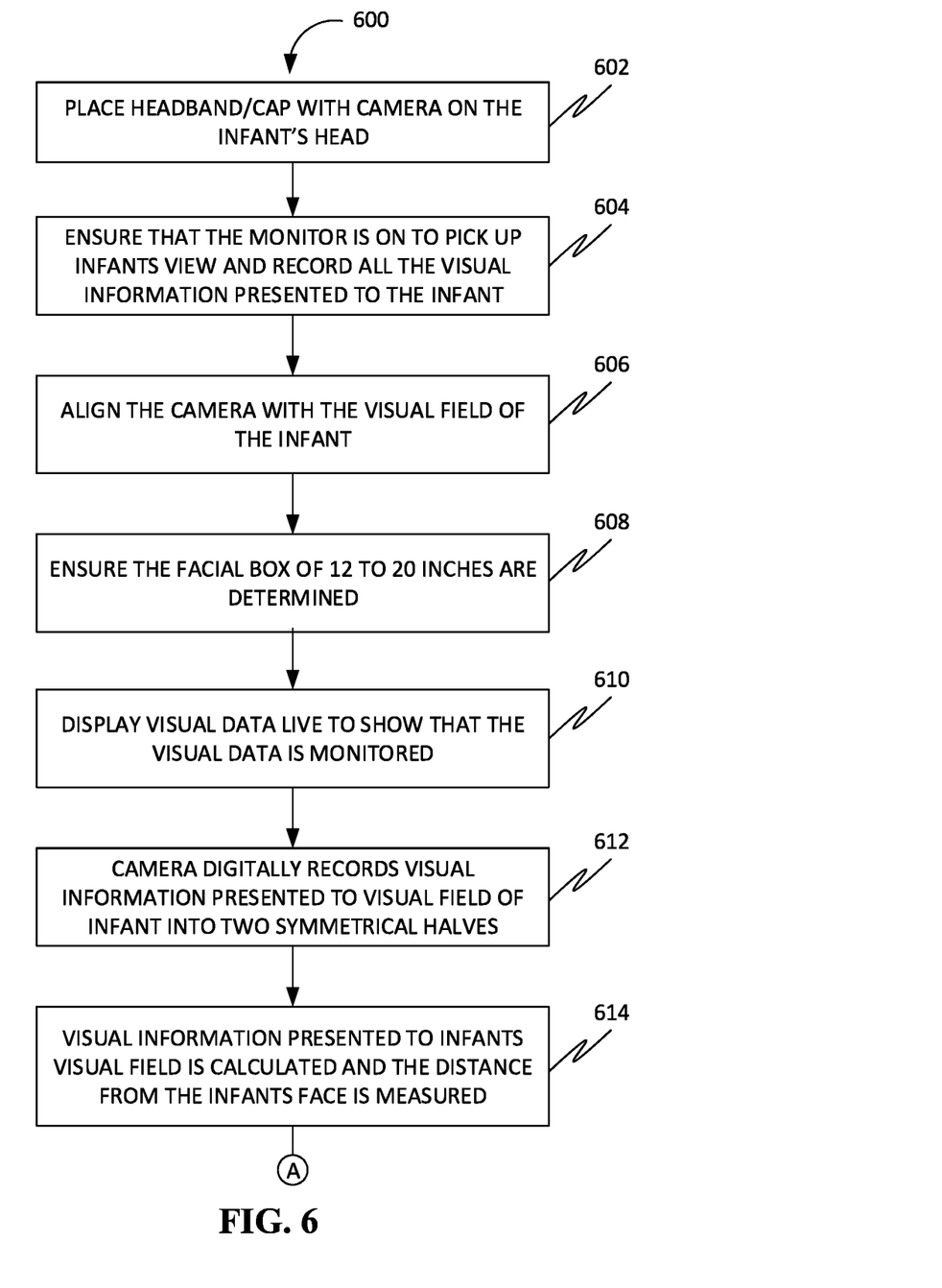
FIG. 6 is a flowchart of a method for monitoring the facial presentation of a first user to a second user, in accordance with some embodiments.

FIG. 6 is a flowchart of a method 600 for monitoring facial presentation of a caregiver (the first user) to an infant (the second user), in accordance with some embodiments. At 602, the method 600 may include placing a headband/cap with camera on an infant's head. The sagittal plane or median plane of the infant anatomy divides the skull into two symmetric halves parallel to sagittal suture line of the skull. The camera on the headband/cap may record the viewpoint of the infant. The camera field of view may be facing directly in front of the infant with vertical midline of field of view aligned with the median plane. The camera may digitally record the visual data presented to visual field of infant.

At 604, the method 600 may include ensuring that the monitor is switched-on to pick up the viewpoint of the infant and record all the visual data presented to the infant. The visual data captured by the camera may be projected onto a monitor (a video screen).

At 606, the method 600 may include aligning the median plane of the caregiver in parallel with the median plane of the infant. The caregiver may be facing the infant with the tip of the caregiver's nose approximately 6-12 inches away from the tip of infant's nose. The frontal or coronal plane of the infant's skull may be parallel with a frontal or coronal plane of the caregiver. This is the face-to-face eye-to-eye and nose-to-nose position.

Further, a check may be performed to confirm if the camera is aligned correctly. While the infant is in the face-to-face eye-to-eye and nose-to-nose position, the digital data may be projected onto the monitor. If alignment is proper, then the vertical midline of the monitor may divide the face of the caregiver into two equal halves along the median plane.

At 608, the method 600 may include ensuring that a facial box at a distance of 12-20 inch is determined. At 610, the method 600 may include displaying visual data live to show that the visual data is monitored. At 612, the method 600 may include recording visual information presented to visual field of infant into two symmetrical halves. Further, at 614, the method 600 may include presenting visual information to the infant's visual field and measuring the distance from the infant's face.

Figure 7:
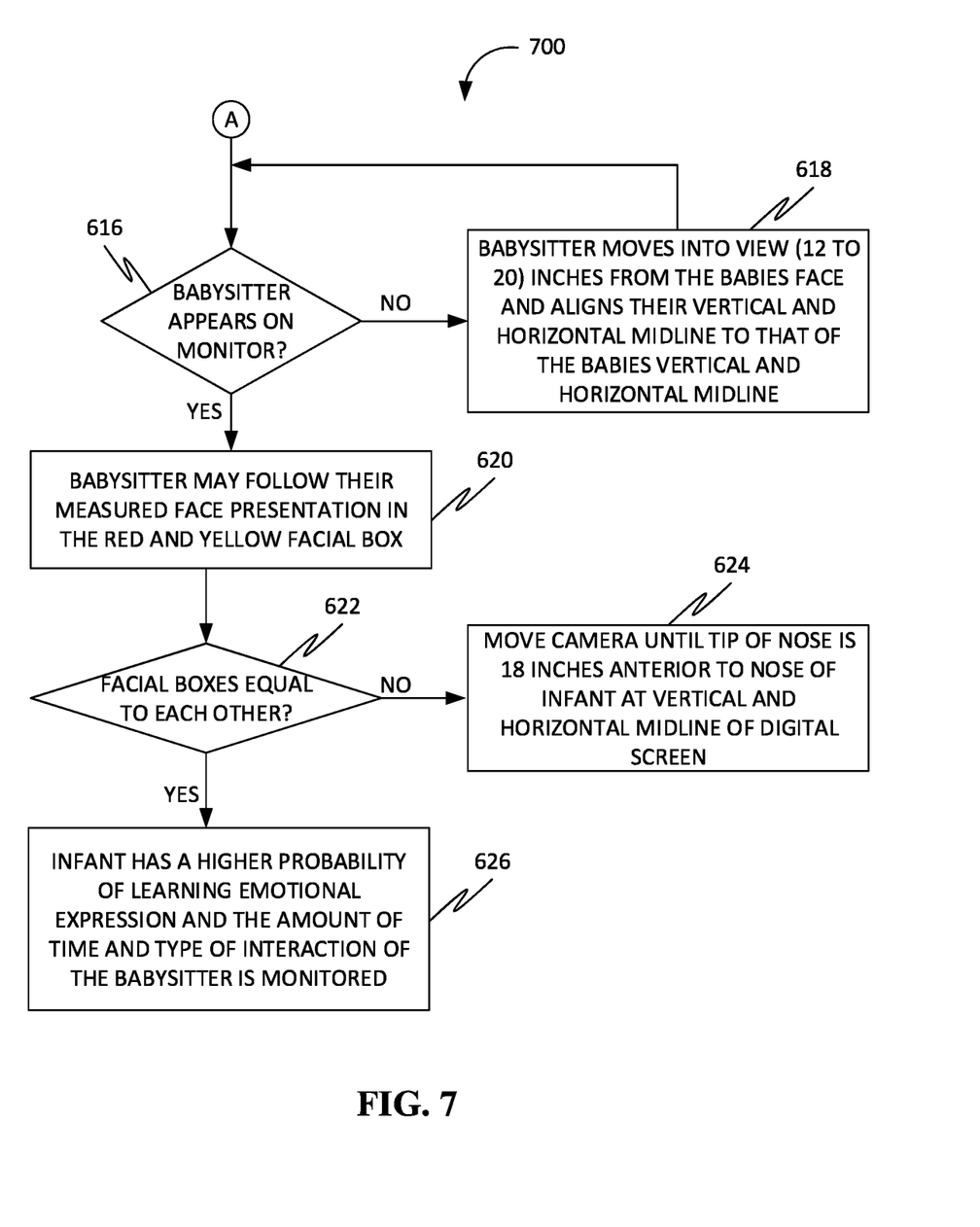
FIG. 7 shows a continuation flowchart of the flowchart shown in FIG. 6.

The flow of the operations of the method 600 then goes on to 616 of a continuation flowchart shown in FIG. 7. At 616, the method 600 may include determining if the caregiver appears on the monitor. If it is determined that the caregiver does not appear on the monitor, then at 618, the method 600 may include moving the caregiver into a view (at a distance of 12-20 inches) of the babies face and aligning their vertical and horizontal midline with that of the babies vertical and horizontal midline.

However, if it is determined that the caregiver appears on the monitor, then at 620, the method 600 may include allowing the caregiver to follow their measured face presentation in a red and yellow facial box.

Then, at 622, the method 600 may include determining if the facial boxes are equal to each other. If it is determined that the facial boxes are not equal to each other, then at 624, the method 600 may include moving the camera until the tip of the nose is 18 inches anterior to the nose of the infant at the vertical and the horizontal midline of the monitor.

However, if it is determined that the facial boxes are equal to each other, then at 626, the method 600 may include determining that the infant has a higher probability of learning emotional expression and the amount of time and type of interaction of the caregiver is monitored.

In further embodiments, the method 600 may include determining the area of image occupied by the face in eye-to-eye position when the eye-to-eye separation is 12 inches. When the infant and the caregiver are properly aligned along the sagittal median plane in the camera image, the eyes of caregiver may be moved 12 inches directly anterior to the eyes of the infant. While eye-to-eye at 12-inch distance the facial recognition analysis may be performed. The facial landmarks of the caregiver's face may occupy a certain area of the camera image. The facial recognition analysis may be capable of creating a facial box of yellow color on the monitor. The facial landmarks may be projected simultaneously and form a box or area on the monitor viewable by the caregiver. The facial box may be in the vertical midline of the monitor. The area of the facial box may occupy an area of the midline of the monitor. The midline of the facial box may align with midline of the monitor. Accordingly, a yellow box may be displayed on the monitor to show facial box at 12-inch distance.

Further, the method 600 may include determining a facial box at infant's arm's length. The infant may be held at arm's length (that is, 18-24 inches) distance between eyes of the infant and the caregiver with the median plane of infant head parallel with the median plane of caregiver. Simultaneously the facial plane or frontal coronal plane of skull may be aligned to be parallel to facial plane of infant. The eyes of infant may be 18 to 24 inches directly anterior to eyes of caregiver. This is the eye-to-eye face-to-face position at arm's length. While in this position, facial recognition may be performed, and a facial box including facial landmarks may be formed. The facial box landmarks at arm's length may be projected onto the digital viewing monitor as a colored box like a red box.

Further, the facial boxes (at 12 inches or the arm's length) may be displayed on monitor even while live video is projected on the monitor. The computer with facial recognition may process data for creating a facial box either on live or recorded digital data and project it on the monitor with the red and yellow facial boxes. The size of the facial box in the image may be determined by face size and distance from the camera. The facial box at arm's length is smaller than the facial box at 12-inch distance. The arm's length facial box may be in the midline of monitor and fit inside the facial box created by face at 12-inch distance. The facial box of the arm's length face (at 20-inch distance) may be smaller and colored by different color such as red color. The red box from face at 20-inch distance may fit inside the yellow facial box. The monitor may retain the yellow box and red box on the monitor for teaching purposes while the caregiver is being graded. The yellow and red boxes may be retained after programming by the caregiver and projected on the monitor. If caregiver is 6 feet away from the infant, the size of the facial box may only be about a third of the size at 20-inch distance.

Further, the facial landmarks may be used to program emotional expression. With the caregiver's face in the yellow box at 12-inch eye-to-eye distance and the red box at 18-22-inch distance, the caregiver may make facial expression. The caregiver may make blank face (an emotionless face). Then caregiver may make a happy face, which may be recorded. Similarly, a sad face may be recorded. The position of the facial landmarks during these expressions may be recorded as well. The facial recognition data may record how often it detects these facial expressions.

Thereafter, a live video with the caregiver's face may be displayed in the infant's point of view. If the caregiver's facial box is smaller than the facial box at arm's length, then the infant is outside of reach of caregiver. An infant that is outside reach of caregiver has less manual influence from caregiver. When facial box of caregiver is within a large facial box at 12-inch distance, then the infant is able to view and process the facial information. The time the yellow box has a live facial box is recorded. The time a caregiver's facial box covers most or all the entire red facial box is recorded. The best facial teaching is when the yellow facial box is at least the size of the red box and covers most or all of the red box. If no live facial box appears then no facial learning may occur. Therefore, only when the live facial box appears within the yellow box or the red box, there is the opportunity to learn facial recognition data.

Figure 8:
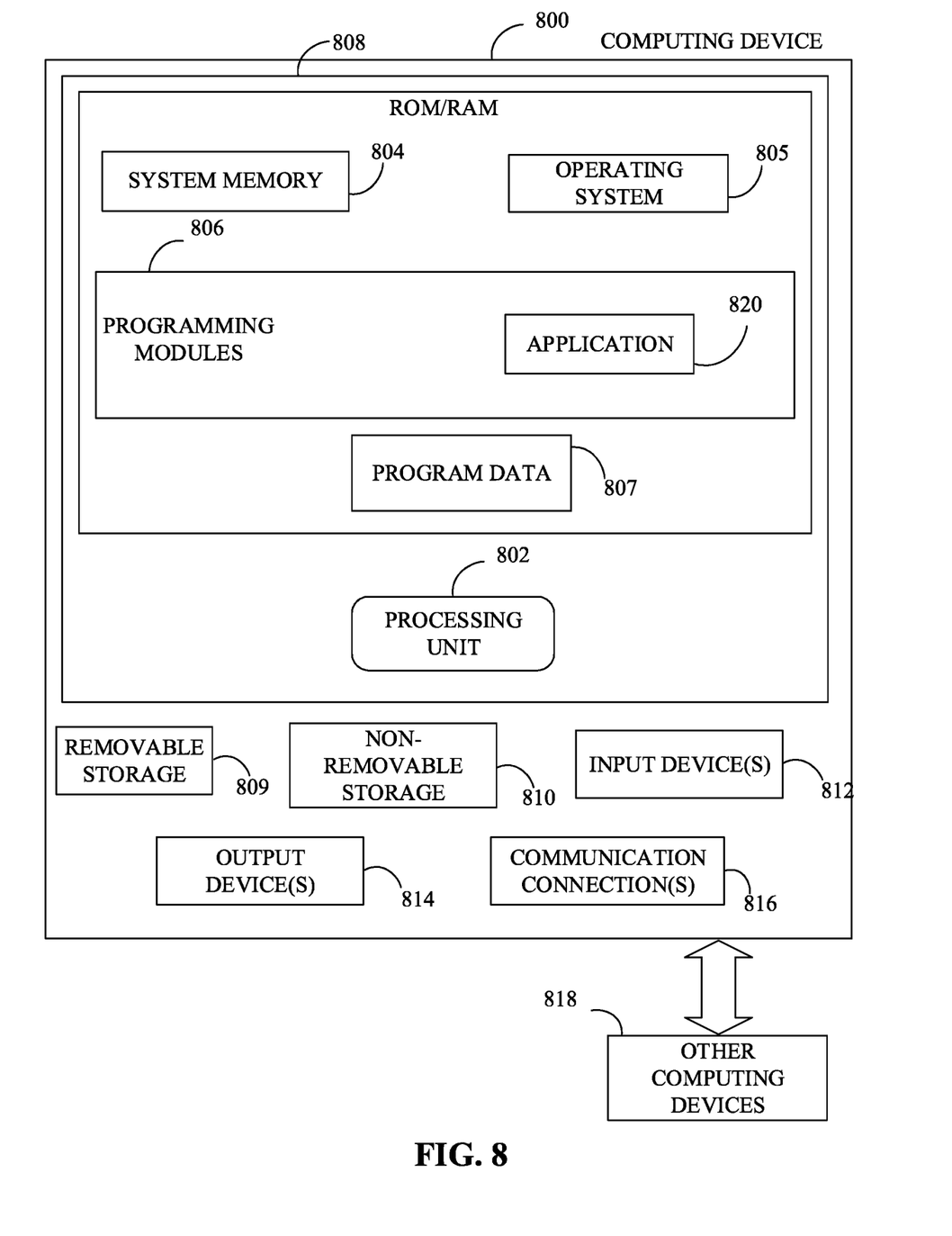
FIG. 8 is a block diagram of a computing device for implementing the methods disclosed herein, in accordance with some embodiments.

With reference to FIG. 8, a system consistent with an embodiment of the disclosure may include a computing device or cloud service, such as computing device 800. In a basic configuration, computing device 800 may include at least one processing unit 802 and a system memory 804. Depending on the configuration and type of computing device, system memory 804 may comprise, but is not limited to, volatile (e.g. random-access memory (RAM)), non-volatile (e.g. read-only memory (ROM)), flash memory, or any combination. System memory 804 may include operating system 805, one or more programming modules 806, and may include a program data 807. Operating system 805, for example, may be suitable for controlling computing device 800's operation. In one embodiment, programming modules 806 may include machine learning module. Furthermore, embodiments of the disclosure may be practiced in conjunction with a graphics library, other operating systems, or any other application program and is not limited to any particular application or system. This basic configuration is illustrated in FIG. 8 by those components within a dashed line 808.

Computing device 800 may have additional features or functionality. For example, computing device 800 may also include additional data storage devices (removable and/or non-removable) such as, for example, magnetic disks, optical disks, or tape. Such additional storage is illustrated in FIG. 8 by a removable storage 809 and a non-removable storage 810. Computer storage media may include volatile and nonvolatile, removable and non-removable media implemented in any method or technology for storage of information, such as computer-readable instructions, data structures, program modules, or other data. System memory 804, removable storage 809, and non-removable storage 810 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 800. Any such computer storage media may be part of device 800. Computing device 800 may also have input device(s) 812 such as a keyboard, a mouse, a pen, a sound input device, a touch input device, a location sensor, a camera, a biometric sensor, etc. Output device(s) 814 such as a display, speakers, a printer, etc. may also be included. The aforementioned devices are examples and others may be used.

Computing device 800 may also contain a communication connection 816 that may allow device 800 to communicate with other computing devices 818, such as over a network in a distributed computing environment, for example, an intranet or the Internet. Communication connection 816 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 804, including operating system 805. While executing on processing unit 802, programming modules 806 (e.g., application 820 such as a media player) may perform processes including, for example, one or more stages of methods, algorithms, systems, applications, servers, databases as described above. The aforementioned process is an example, and processing unit 802 may perform other processes. Other programming modules that may be used in accordance with embodiments of the present disclosure may include data processing application, machine learning application, etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the disclosure has been explained in relation to its preferred embodiment, it is to be understood that many other possible modifications and variations can be made without departing from the spirit and scope of the disclosure.

What is claimed is:

1. A system for monitoring facial presentation of a first user to a second user, the system comprising:
   at least one image capturing device configured for capturing at least one image of the first user;
   a communication device communicatively coupled to the at least one image capturing device, wherein the communication device is configured for transmitting the at least one image to a processing device;
   the processing device communicatively coupled to the communication device, wherein the processing device is configured for:
   analyzing the at least one image;
   identifying a face of the first user based on the analyzing; and
   generating facial presentation data based on the identifying;

a storage device configured for storing the facial presentation data;
wherein the facial presentation data comprises an area of a visual field corresponding to the at least one image capturing device, wherein the area is occupied by the face of the first user;
wherein the facial presentation data comprises a time period corresponding to the absence of the face of the first user in the visual field;
wherein the processing device is further configured for:
analyzing the facial presentation data based on at least one predefined criterion, wherein the at least one predefined criterion is a threshold time period; and
generating an alert in response to the time period being over the threshold time period based on the analyzing; and
wherein the communication device is further configured for:
transmitting the alert to a user device.

2. The system of claim 1, wherein the at least one image capturing device is comprised in a wearable article configured to be worn by at least one of the first user and the second user.

3. The system of claim 1, wherein the at least one image capturing device is configured to be disposed proximal to at least one eye of the second user.

4. The system of claim 1, wherein the at least one image capturing device is configured to be disposed in the median plane of the second user.

5. The system of claim 1, wherein the facial presentation data comprises a time duration corresponding to the presence of the face of the first user in the visual field.

6. The system of claim 1, wherein the facial presentation data comprises a location of the face of the first user within the visual field.

7. The system of claim 1, wherein the facial presentation data comprises an orientation of the face of the first user within the visual field.

8. The system of claim 1, wherein the facial presentation data comprises an alignment indicator based on alignment between the face of the first user and a face of the second user.

9. The system of claim 1, further comprising: identifying at least one emotional expression associated with the face of the first user based on the analyzing, wherein the facial presentation data comprises the at least one emotional expression.

10. The system of claim 9, wherein the processing device is further configured for determining at least one frequency corresponding to the at least one emotional expression, wherein the facial presentation data comprises the at least one frequency.

11. The system of claim 1 further comprising: a distance sensor configured to measure a distance between the first user and the second user, wherein the generating of the facial presentation data is based further on the distance.

12. The system of claim 1 further comprising: a display device communicatively coupled to the processing device, wherein the display device is configured to display at least one of the at least one image of the first user and the facial presentation data.

13. The system of claim 1, wherein the facial presentation data comprises at least one facial landmark.

14. The system of claim 1, wherein the processing device is further configured for generating an audible message based on the facial presentation data, wherein the communication device is configured for transmitting the audible message to a user device associated with the first user.

15. The system of claim 1 further comprising: at least one display device configured to be communicatively coupled to the communication device, wherein the display device is further configured to be disposed on the second user, wherein the display device is configured to display the facial presentation data.

16. The system of claim 1, wherein the facial presentation data comprises the face of the first user, wherein the processing device is further configured for:
identifying at least one non-facial portion of the first user in the at least one image; and
redacting the at least one image based on the identifying of the at least one non-facial portion; and
generating at least one redacted image based on the redacting, wherein the storage device is further configured for storing the at least one redacted image.

17. The system of claim 1, wherein the at least one image capturing device is further configured for capturing at least one image of the second user, wherein the processing device is further configured for:
analyzing the at least one image of the second user;
identifying a face of the second user based on the analyzing of the at least one image of the second user; and
generating facial response data based on the identifying of the face of the second user, wherein the storage device is further configured for storing the facial response data.

18. The system of claim 17, wherein the processing device is further configured for:
comparing the facial presentation data with the facial response data; and
diagnosing a behavioral disorder based on the comparing.

* * * * *